United States Patent
Gebeyehu et al.

(10) Patent No.: US 7,531,693 B2
(45) Date of Patent: May 12, 2009

(54) LIPIDS FOR TRANSFECTION OF NUCLEIC ACIDS

(75) Inventors: Gulilat Gebeyehu, Potomac, MD (US); Taysir M. Jaouni, Hagerstown, MD (US); Joel Jessee, Mount Airey, MD (US)

(73) Assignee: Molecular Transfer, Inc., Gaithersburg, MD (US)

( * ) Notice: Subject to any disclaimer, the term of this patent is extended or adjusted under 35 U.S.C. 154(b) by 600 days.

(21) Appl. No.: 10/851,658

(22) Filed: May 24, 2004

(65) Prior Publication Data

US 2005/0014962 A1    Jan. 20, 2005

Related U.S. Application Data

(60) Provisional application No. 60/472,403, filed on May 22, 2003.

(51) Int. Cl.
*C07C 215/00* (2006.01)
*A61K 31/45* (2006.01)

(52) U.S. Cl. ............... 564/503; 564/292; 564/294; 564/295; 564/504; 564/505; 564/506; 564/507; 564/508; 514/663

(58) Field of Classification Search .............. None
See application file for complete search history.

(56) References Cited

U.S. PATENT DOCUMENTS

| 2,636,051 | A | * | 4/1953 | Whetstone et al. | .......... 564/473 |
| 5,264,618 | A | | 11/1993 | Felgner et al. | |
| 5,334,761 | A | | 8/1994 | Gebeyehu et al. | |
| 5,753,613 | A | | 5/1998 | Ansell et al. | .......... 514/2 |
| 5,777,153 | A | | 7/1998 | Lin et al. | .......... 560/159 |
| 6,235,310 | B1 | | 5/2001 | Wang et al. | .......... 424/450 |

FOREIGN PATENT DOCUMENTS

WO    WO 00/27795 A1    5/2000

OTHER PUBLICATIONS

Database CAPLUS on STN, Acc. No. 1952:60760, GB 663294 (Dec. 19, 1951) (astract).*
Behr et al., *Proc. Nat'l. Acad. Sci.*, 86:6982 (1989).
Benerjee et al., *J. Med. Chem.*, 44:4176 (2001).
Felgner et al., *Proc. Nat'l Acad. Sci.*, 84:7413 (1987).
International Search Report dated Oct. 10, 2006.

* cited by examiner

*Primary Examiner*—Brian J Davis
(74) *Attorney, Agent, or Firm*—Proskauer Rose LLP

(57) ABSTRACT

Cationic lipid compositions are provided that are useful for efficient delivery of macromolecules, such as nucleic acids, into a wide variety of eukaryotic cell types. Methods for using the compositions also are provided.

27 Claims, 5 Drawing Sheets

FIGURE 1: Transfection of COS 7 with pCMV-Sport β-gal and MT-R1, MT-R2, MT-R3 and LipofectAMINE 2000 (L2K)

FIGURE 2: Transfection of VERO with pCMV-Sport β-gal using MT-R1 and commercial cationic lipids.

FIGURE 3: Transfection of BHK-21 with pMCMV-Sport β-gal MT-R2 and lipofectamine 2000

Scheme 1: Generalized synthesis of cationic glycolipid analogs

Scheme 2 : Synthesis of alkylaminoalcohol lipids

LIPIDS FOR TRANSFECTION OF NUCLEIC ACIDS

This application claims priority to application Ser. No. 60/472,403, filed May 22, 2003, the contents of which are incorporated herein in their entirety.

BACKGROUND OF THE INVENTION

The use of cationic lipids to deliver nucleic acids into cultured cells was first described by Felgner and co-workers (*Proc. Nat'l Acad. Sci.* 84,7413 (1987)). Subsequently, Behr (*Proc. Nat'l Acad. Sci.* 86, 6982 (1989)) showed that polycationic lipids also can be effective delivery agents. Large number of cationic lipid reagents have now been described and several of these reagents are commercially available, for example, LipofectAmine, LipofectAmine 2000, Fugene, TransfectAm, Lipofectin and DOTAP. None of these reagents, however, is universally effective on all cell lines and none is as effective as viral based gene delivery systems. In addition, most of the reagents are toxic in some degree to the cells being transfected.

Accordingly, there still exists a great need for the development of transfection reagents that are less toxic than those currently available but that are highly efficient and more universally applicable for transfecting a wide variety of cell types. Ideally, such a reagent will have minimal safety risk and immunogenicity when compared to viral based delivery systems. The successful development of such a reagent will have a profound impact in biotechnology in general and gene therapy in particular.

SUMMARY OF THE INVENTION

It is therefore an object of the invention to provide novel compositions that are useful for delivery of macromolecules, such as nucleic acids, into cells.

It is a further object of the invention to provide methods of using these compositions to deliver macromolecules, such as nucleic acids, into cells.

In accomplishing these objects, there is provided, in accordance with a first aspect of the invention, a lipid having the formula:

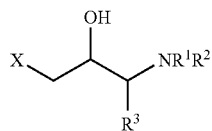

wherein X is $N(R^4R^5R^6)$ or dialkylphosphatidyl, or X is

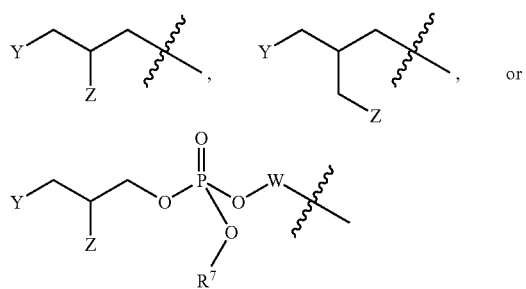

Y and Z independently are selected from the group consisting of alkoxy, alkanoyloxy, alkylamine, alkyl urethane and alkyl guanidine $R^1$ and $R^2$ independently are selected from the group consisting of hydrogen, $C_1$-$C_6$ alkyl, alkylamine, alkylaminoalcohol, spermiyl, spermidyl and carboxyspermiyl, $R^3$ is H or $C_1$-$C_4$ alkyl, $R^4$, $R^5$, and $R^6$ independently are selected from the group consisting of hydrogen, alkyl, alkenyl, aryl and alkylaryl, provided that at least one of $R^4$, $R^5$, and $R^6$ is a long chain alkyl or alkenyl, W is short chain alkyl or alkylamino, and $R^7$ is a negative charge or short chain alkyl.

In accordance with a second aspect of the invention there is provided a lipid having the formula:

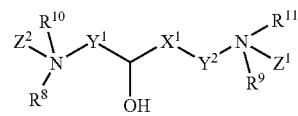

wherein $X^1$ is selected from the group consisting of $(CH_2)_n$, $(CHOH)_n$, —NH—, —O—, a polyether, an ester linkage —S—, CONH, NHCO, a polyamide —NHCONH—, and NHC (=NH) NH, wherein $Y^1$ is selected from the group consisting of $(CH_2)_n$, a polyether, NHCO, —CO—, and a polyamide, wherein $Y^2$ is selected from the group consisting of $(CH_2)_n$, —NH—, —O—, a polyether, an ester linkage, —S—, CONH, NHCO, a polyamide —NHCONH—, and NHC (=NH) NH, wherein $Z^1$ and $Z^2$ are independently selected from the group consisting of hydrogen, primary alkylamine, secondary alkylamine, tertiary alkyl amine, quaternary alkylamine, alkyl amino alcohol, alkyl polyamine, spermidine, spermine, carboxy spermine, guanidinium, pyridinium, pyrollidinium, piperidinyium amino acyl, peptidyl, and protein, $R^8$, $R^9$, $R^{10}$, and $R^{11}$ are independently absent or are selected from the group consisting of hydrogen, straight chain $C_1$-$C_{20}$ alkyl, branched alkyl, cyclalkyl, straight chain alkenyl, branched alkenyl, cyclo alkenyl, and optionally substituted aryl, wherein said optional substitution, when present, comprises at least one functional group selected from the group consisting of —OH, $NH_2$, —COOH, ester, amide, alkylamino, —NHCONH—, and NHC (=NH) NH], and wherein n=1-12.

In one embodiment, there is provided a composition comprising a lipid as described above, and one or more macromolecules, such as one or more peptides, proteins and/or nucleic acids. The nucleic acid may comprise a DNA molecule, for example a double stranded DNA molecule. The DNA molecule may be a plasmid, and may encode, for example, an RNA molecule that is self complementary and that forms a region of double stranded RNA.

In another embodiment, the nucleic acid may comprise one or more RNA molecules, for example, one or more double stranded RNA molecules. The RNA molecule may be an siRNA.

In accordance with another aspect of the invention there is provided a method of introducing a peptide, protein, and/or nucleic acid into a cell or a tissue, by contacting a eukaryotic cell or tissue with a composition as described above.

In accordance with yet another aspect of the invention there is provided a kit for transfecting a cell, comprising a lipid as described above.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1:
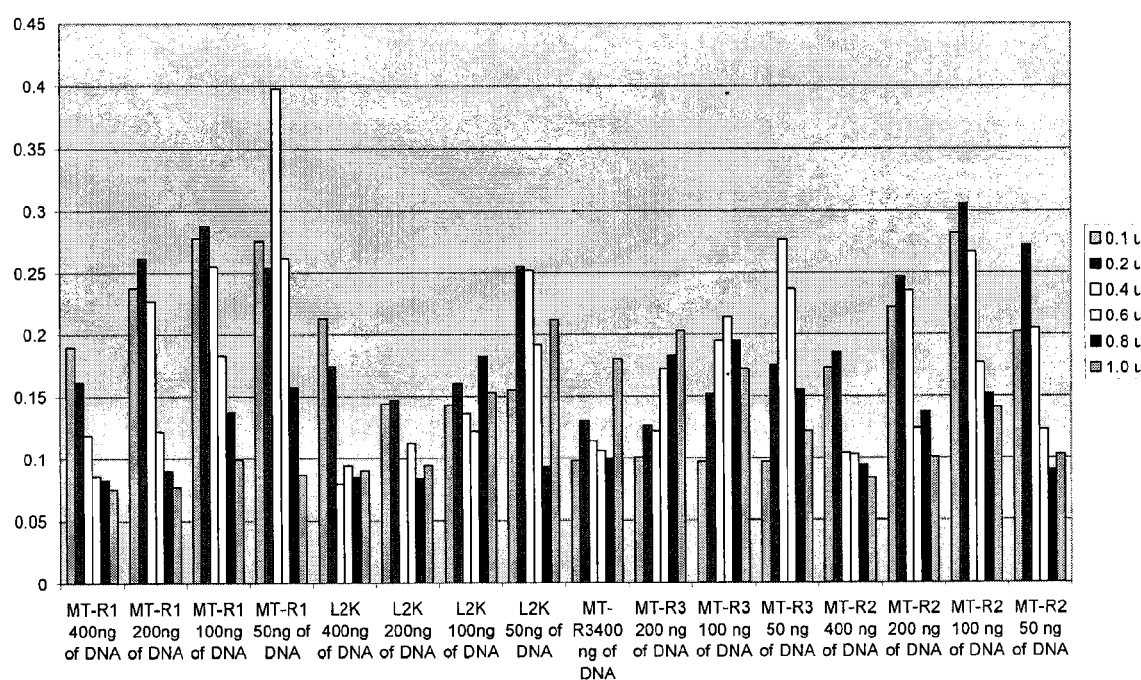
FIG. 1 shows the results obtained from transfection of COS 7 cells with pCMV-Sport β-gal and MT-R1, MT-R2, MT-R3 and LipofectAMINE 2000 (L2K).

The present invention provides novel lipids that are effective for the introduction of nucleic acids and peptides and proteins into a wide variety of cells and tissues. The lipids are highly efficient and demonstrate low toxicity in all cell types tested. The lipids have the general structures I and II shown below.

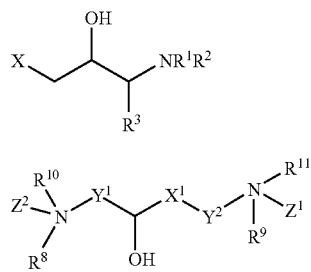

The compounds of formula I contain an amino alcohol head group, and X may be $N(R^4R^5R^6)$ or dialkylphosphatidyl, or X may be

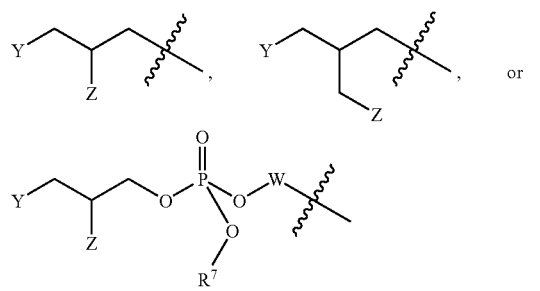

Y and Z independently may be selected from the group consisting of alkoxy, alkanoyloxy, alkylamine, alkyl urethane and alkyl guanidine. $R^1$ and $R^2$ independently may be selected from the group consisting of hydrogen, $C_1$-$C_6$ alkyl, $C_1$-$C_6$ alkylamine, alkylaminoalcohol, spermiyl, spermidyl and carboxyspermiyl. $R^3$ is H or $C_1$-$C_4$ alkyl. $R^4$, $R^5$, and $R^6$ independently are selected from the group consisting of hydrogen, alkyl, alkenyl, aryl, and alkylaryl, provided that at least one of $R^4$, $R^5$, and $R^6$ is a long chain alkyl or alkenyl. The alkyl, alkenyl, aryl, and alkylaryl groups may contain, for example, 6 to 30 carbon atoms, advantageously 10 to 18 carbon atoms, although the skilled artisan will recognize that the groups may contain fewer than 6 or more than 30 carbon atoms. W may be short chain ($C_1$-$C_6$) alkyl or alkylamino, and $R^7$ may be a negative charge or short chain ($C_1$-$C_6$) alkyl. Representative examples of compounds encompassed by general formula I include compounds 12 and 13 shown below, where for example, R is oleyl.

In compounds of formula II, which contain hydrocarbon moieties conjugated to simple carbohydrates, $X^1$ may be selected from the group consisting of $(CH_2)_n$, $(CHOH)_n$, —NH—, —O—, a polyether, an ester linkage —S—, CONH, NHCO, a polyamide —NHCONH—, and NHC (=NH) NH. $Y^1$ may be selected from the group consisting of $(CH_2)_n$, a polyether, NHCO, —CO—, and a polyamide. $Y^2$ may be selected from the group consisting of $(CH_2)_n$, —NH—, —O—, a polyether, an ester linkage, —S—, CONH, NHCO, a polyamide —NHCONH—, and NHC (=NH) NH. $Z^1$ and $Z^2$ may independently be selected from the group consisting of primary alkylamine, secondary alkylamine, tertiary alkyl amine, quaternary alkylamine, alkyl amino alcohol, alkyl polyamine, spermidine, spermine, carboxy spermine, guanidinium, pyridinium, pyrollidinium, piperidinyium amino acyl, peptidyl, and protein. $R^8$, $R^9$, $R^{10}$, and $R^{11}$ independently may be absent or may be selected from the group consisting of hydrogen, straight chain $C_1$-$C_{20}$ alkyl, branched alkyl, cyclalkyl, straight chain alkenyl, branched alkenyl, cyclo alkenyl, and optionally substituted aryl, where the optional substitution, when present, comprises at least one functional group selected from the group consisting of OH, $NH_2$, —COOH, ester, amide, alkylamino, —NHCONH—, and NHC (=NH) NH], and n is an integer from 1 to 12.

In the context of the present invention, a short chain alkyl group is typically, unless otherwise defined, $C_1$-$C_6$ alkyl, for example. A long chain alkyl group is typically, unless otherwise defined, $C_{10}$-$C_{20}$ alkyl, for example, or $C_{10}$-$C_{30}$ alkyl. When not specifically defined, either definition may be used, as appropriate. The skilled artisan also will appreciate that other derivative groups containing alkyl moieties, for example, alkoxy moieties and the like, also may contain short and/or long chain groups as appropriate in the context, unless otherwise defined.

Molecules of formulas I and II may be prepared by methods that are well known in the art. See, for example, U.S. Pat. Nos. 5,334,761 and 5,264,618, WO00/27795 and Benerjee et al. (*J. Med. Chem.*, 44, 4176 (2001), which references are hereby incorporated by reference in their entireties.

Figure 4:
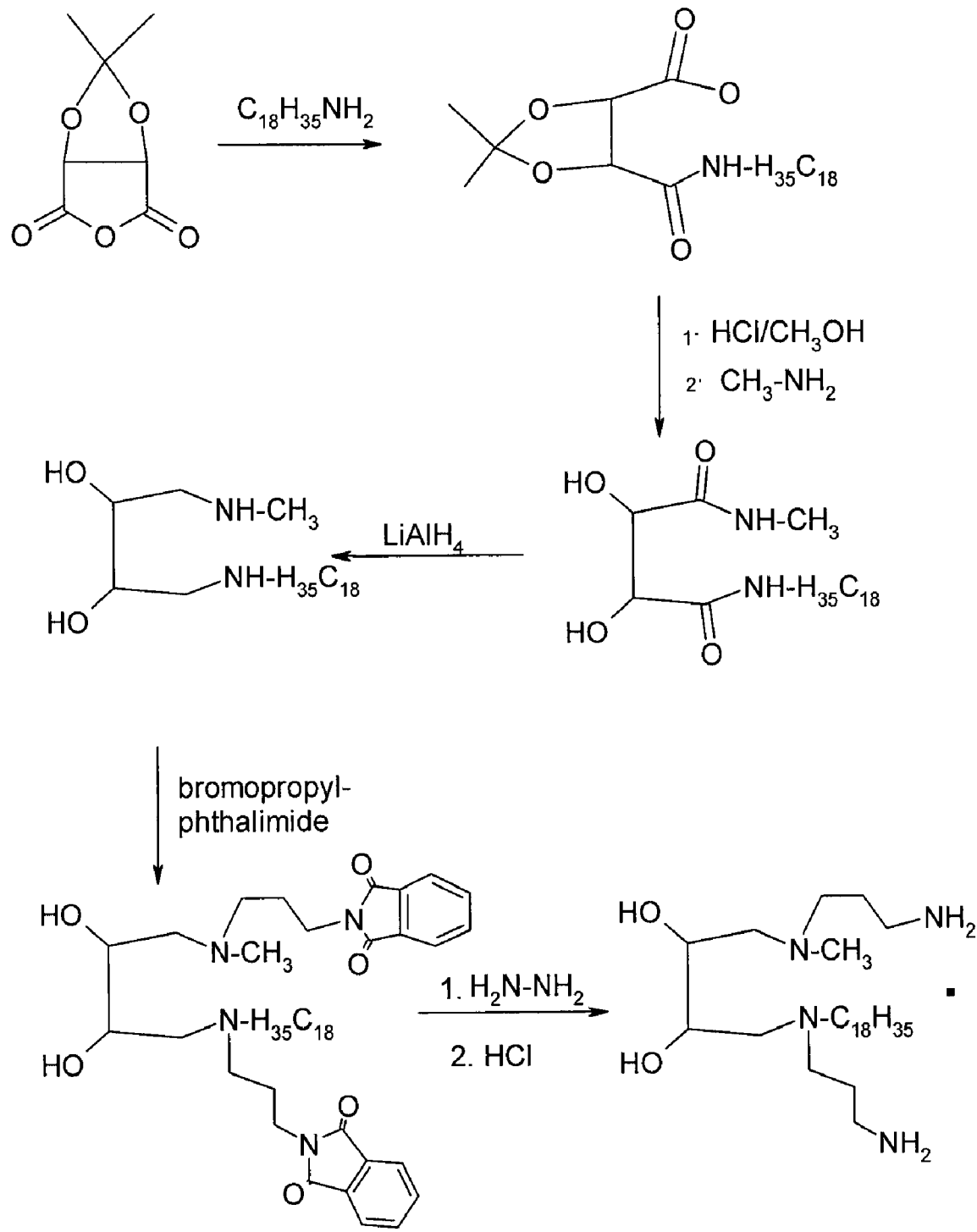
FIG. 4 shows a generalized synthesis of cationic glycolipid analogs

Specific methods are shown below for the synthesis of representative members of both classes of lipids (see Scheme 1 and Scheme 2 in FIGS. 4 and 5). The skilled artisan will recognize that other members of these lipid classes can be synthesized using variations of these methods or by other methods that are well known in the art.

Preparation of the Lipids

Synthesis of the cationic glycolipids (II) may be achieved via the methods outlined in Scheme 1 (FIG. 4). 2,3-Isopropylidine tartaric anhydride is treated with an alkylamine, such as oleoyl amine, to ring-open the anhydride and generate the corresponding amide and carboxylic acid. Treatment of the amide with acidic methanol results in the removal of the isopropylidine group and esterification of the acid. The ester is treated with alkylamine such as methylamine to obtain the corresponding diamide. The diamide is reduced to the diamine with a reducing agent such as lithium aluminum hydride and alkylated with alkylating agents such as bromopropylphthalimide. The phthalimide group is removed with hydrazine and the amine protonated with HCl to obtain the desired cationic lipid. This scheme can be effectively used to synthesize specific compounds of the general structure 1-[(3-aminopropyl)-alkyl$^1$amino]-4-[(3-aminopropyl)-alkyl$^2$amino]-butane-2,3-diol when bromopropylphthalamide is used as the alkylating agent or 1-[(3-amino-2-hydroxypropyl)-alkyl$^1$amino]-4-[(3-amino-2-hydroxypropyl)-alkyl$^2$amino]-butane-2,3-diol. Alkyl$^1$ can be methyl, ethyl, propyl, $C_{10}$-$C_{20}$ alkyl chain and alkyl$^2$ can be a $C_{10}$-$C_{20}$ alkyl chain.

Alternatively, the symmetrical analogs of the cationic glycolipids can be obtained starting with the amidation of the methyl ester of a desired diacid ($HO_2C$—$(CHOH)_n$—$CO_2H$, n=2-6) such as dimethyltartarate with a desired alkyl amine. The diamide is reduced using a suitable reducing agent, such as lithium aluminum hydride, to generate the corresponding amine. The amine groups may be alkylated with bromopropyl phthalimide or epoxypropyl phthalimide, followed by removal of the phthalimide group with hydrazine hydrate to obtain the desired cationic lipid. This synthetic route is generally applicable to all compounds of general formula 1,4-bis[(3-amino-propyl)alkylamino]-butane-2,3-diol when bromopropyl phthalimide is used as the alkylating agent, and 1,4-bis[(3-amino-2-hydroxypropyl)alkylamino]-butane-2,3-diol when epoxypropylphthalamide is used as the alkylating agent. The alkyl group can constitute a $C_{10}$-$C_{20}$ alkyl chain. Various glycolipids can obtained by starting with other alderic acids $HO_2C$—$(CHOH)_n$—$CO_2H$ where n=2-6. Representative compounds may be formulated into liposome alone or with co-lipids (DOPE or cholesterole) and used in transfection.

Figure 5:
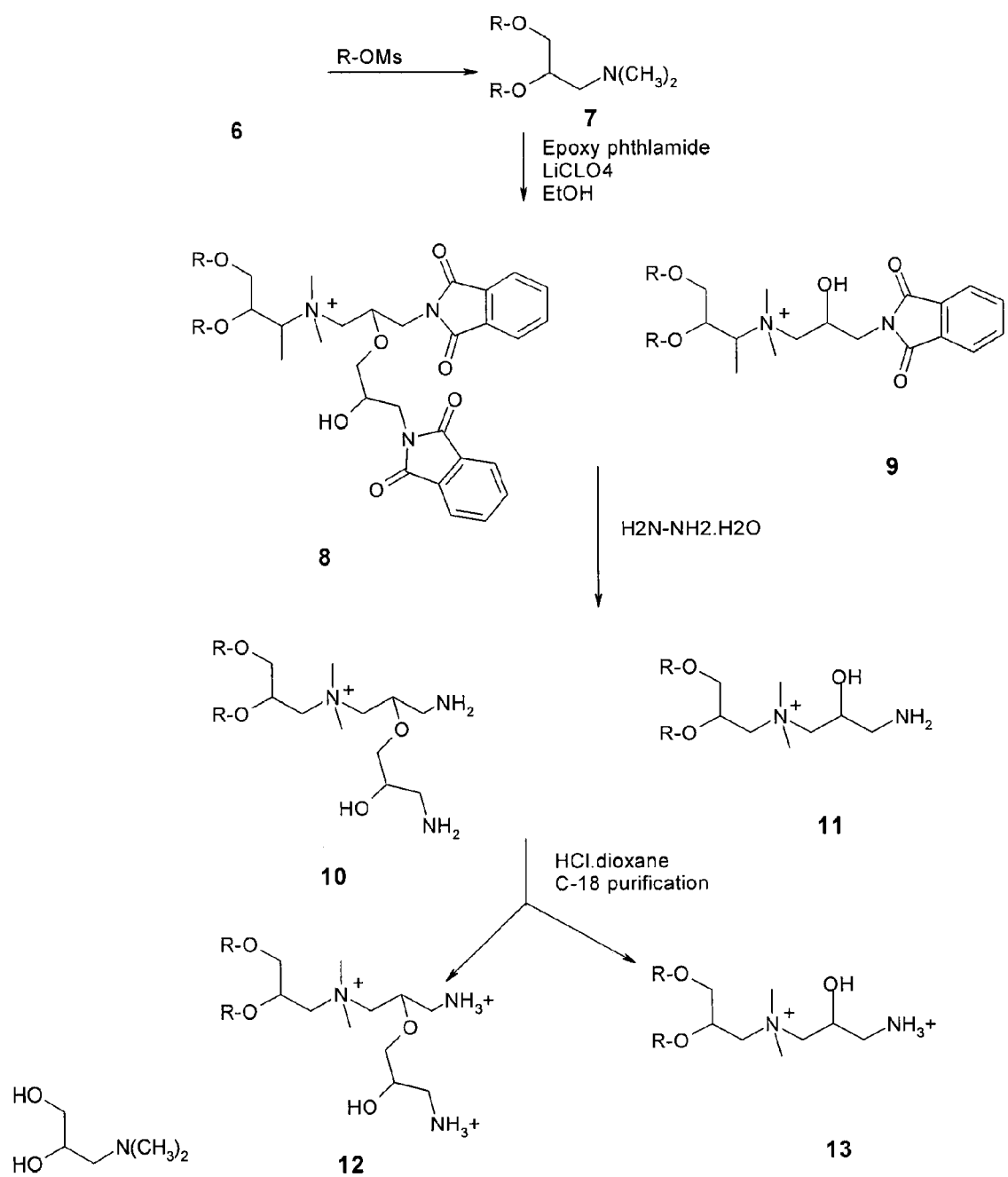
FIG. 5 shows a synthesis of alkylaminoalcohol lipids

Lipids of formula I having an amino alcohol head group may be synthesized as shown in Scheme 2 (FIG. 5). Dimethylaminopropane diol can be alkylated with a desired alkyl sulfonate to produce dialkyloxy-dimethyaminopropane. Further alkylation of dialkyloxy-dimethylaminopropane, to quaternize the amine group, with epoxypropyl phthalimide and the removal of the phthalimide protecting group with hydrazine hydrate provides the desired aminoalcohol as the major product, together with a minor product derived from alkylation of the hydroxide group. Both compounds were protonated with HCl and formulated into liposome alone or with co-lipid (cholesterol or DOPE) and used in transfection.

Cell Transfections Using the Lipids.

The novel lipids described herein may be formulated with one or more nucleic acids into liposomes or liposome-like vehicles in the presence or absence of co-lipid such as dioleoylphosphatidyl ethanolamine (DOPE) or cholesterol. The lipids may be formulated into liposomes by the method of reverse evaporation, which is well known in the art. Alternatively the lipids may be formulated by other well known methods for liposome formation such as sonication, microfluidization etc. These liposome formulations are effective for transfecting DNA into cultured cells.

The lipids are at least as active, and in most cases more active, than cationic lipids that currently are commercially available. The nucleic acid can be any type of nucleic acid that is known, provided that the nucleic acid is sufficiently negatively charged to form a lipid aggregate, liposome, or liposome-like complex when admixed with the lipid. The nucleic acid can be, for example, DNA or RNA, and can be an oligonucleotide, plasmid, or other form of nucleic acid molecule. The nucleic acid may be, without limitation, an antisense molecule, or may be a double stranded RNA molecule of the type used for inhibiting gene expression by RNA interference. The nucleic acid may be a short interfering double stranded RNA molecule (siRNA).

The lipids may also be used to introduce peptides and proteins and the like into cells using methods that are known in the art. Methods of using cationic lipids for peptide and protein delivery previously have been described.

In addition, the lipids may be used to deliver nucleic acids, peptides and proteins and the like into tissues in vivo. Methods of using lipids for delivering compounds to tissue in vivo previously have been described.

Liposome formulations derived from the above compounds were evaluated for transfection efficiency of cultured cells such as BHK-21, HeLa, COS-7, CHO-K1, VERO and 293 with β-galactosidase reporter plasmid pCMV●SPORT-β-gal as described below.

The present invention, thus generally described, will be understood more readily by reference to the following examples, which are provided by way of illustration and are not intended to be limiting of the present invention.

EXAMPLE 1

Synthesis of N-1-dimethyl-N-1-(2,3-ditetradecyloxypropyl)-2-hydroxypropane-1,3-diamine (13)

3-(Dimethylamino)-1,2-Propanediol (10.19 g, 85 mmole) was treated with 2.5 equivalents of sodium hydride in tetrahydrofuran for a 18-24 hour period at 70°±5° C. After 18-24 hour, 3 equivalents of tetradecylmethane sulfonate (75.0 g, 256 mmole) was added to the reaction and allowed to reflux (70°±5° C.) for an additional 40-48 hours. The reaction mixture was concentrated to dryness and subjected to extraction using dichloromethane and water. The organic layer was dried over sodium sulfate and concentrated to an oil on a rotary evaporator. The resulting residue was loaded on a normal phase flash chromatography column and the desired product, 1-dimethylamino-2,3-ditetradecyloxypropane, was purified using ethyl acetate/hexane as the eluant. The final product was analyzed by TLC.

1-Dimethylamino-2,3-ditetradecyloxypropane (15.0 g, 29.35 mmole) was treated with two equivalents of N-(2,3-epoxypropyl)-phthalimide (11.93 g, 58.7 mmoles) and two equivalents of lithium perchlorate (6.245 g, 58.7 mmole) using ethanol as a solvent. The reaction was performed at 75-80° C. for a 96±6 hour period. The reaction was monitored for completeness and formation of desired products 1(N,N-dimethyl-N(2-hydroxy-3-phthalimido-propyl)-ammonium-2,3,-ditetradecyloxypropane. The reaction mixture was concentrated to dryness and extracted using dichloromethane and water. The organic layer was dried over sodium sulfate and concentrated on a rotary evaporator. The resulting reaction mix was loaded on a normal phase flash chromatography column and the desired product 1-(N,N-dimethyl-N-(2-hydroxy-3-phthalimido-propyl)-ammonium-2,3,-ditetradecyloxypropane was purified along with the O-alkylated byproduct using chloroform/methanol as the eluant. The mixture (14.95 g) was reacted with hydrazine hydrate (4.6 ml) using ethanol as a solvent at 75-80° C. for 15-18 hours. The reaction was placed at 4° C. for an overnight period and the precipitate was filtered off. The filtrate was subjected to rotary evaporation which resulted in a gummy material composed of a mixture of two compounds. The residue was dissolved in tetrahydrofuran and acidified using 1.1 equivalents of hydrochloride acid for 1 hour at room temperature. The reaction was dried down and co-evaporated twice with methanol and twice with dichloromethane. The two compounds were purified by reverse phase (C-18) flash chromatography using methanol/water as the solvent. The compounds were characterized by TLC and mass spectrometry as N-1-dimethyl-N-1-(2,3-ditetradecyloxypropyl)-2-hydroxypropane-1,3-diamine (major) and N-1-dimethyl-N-1-(2,3-ditetradecyloxypropyl)-2-(3-amino-2-hydroxypropyloxy)-propane-1,3-diamine (minor)

EXAMPLE 2

Synthesis of 1-[(3-amino-2-hydroxypropyl)-alkylamino]-4-[(3-amino-2-hydroxypropyl)-alkylamino]-butane-2,3-diol or 1,4-Bis[(3-amino-2-hydroxypropyl)-alkylamino]-butane-2,3-diol Dimethyl tartrate (8.2 g, 46.6 mmoles) was dissolved in 150 ml methanol and 1-alkylamine (0.11 mole) was added. The solution was heated to reflux overnight (>22 hrs). The reaction mix was cooled to room temperature and kept at 4° C. for about 1 hour. The precipitate was filtered, and washed twice with 50 ml of cold methanol (<4° C.) to obtain dialkyltartaramide as a white crystalline material (>80%). The product was characterized by TLC and mass spectrometry.

The dialkyltartaramide (29.6 mmole) was suspended in 500 ml anhydrous THF and 200 ml of 1 M lithium aluminium hydride solution in THF was added drop-wise. After the addition was completed, the reaction mix was refluxed overnight. The mixture was cooled and diluted with 500 ml THF. 200 ml of 15% NaOH solution was added drop-wise to the mixture and stirred overnight. The THF layer was decanted and the remaining suspension was exhaustively extracted with chloroform using TLC to monitor the presence of the desired product in the chloroform layer. The organic layer was combined to obtain compound 1,4-bis(alkyl-amino)-butane-2,3-diol as a semi-solid (40-75% yield). The product was characterized by mass spectrometry.

1,4-Bis(alkyl-amino)-butane-2,3-diol (21.87 mmoles) was treated with N-(2,3-epoxypropyl)-phthalimide (10.90 g, 53.69 mmole) and lithium perchlorate (5.63 g, 53.6 mmole) in 500 ml 10% reagent alcohol. The mixture was refluxed overnight and the reaction volume was reduced to 100 ml using the rotary evaporator. The reaction mix was cooled and diluted with 500 ml chloroform. The chloroform solution was extracted twice with 300 ml sodium bicarbonate solution (0.1 M) and once with 300 ml concentrated NaCl solution. The chloroform was removed on the rotary evaporator to obtain the bis-phthalimide adduct as a gum. The compound was characterized by mass spectrometry.

Hydrazine hydrate (2 ml) was added to a solution of the phthalimide in 100 ml of 100% reagent alcohol. The reaction mix was refluxed overnight and cooled to room temperature for about 1 hr. The reaction mix was then cooled at 4° C. overnight and the precipitate filtered off. The solid was washed twice with 20 ml chilled ethanol (−20° C.). The ethanol was removed on the rotary evaporator. The solid was dissolved in chloroform, filtered and extracted with 200 ml water. The chloroform was removed on the rotary evaporator to give a quantitative yield of the desired compound, 1,4-bis[(3-amino-2-hydroxy-propyl)-alkyl-amino]-butane-2,3-diol. This material was purified on reverse phase (C-18) flash chromatography using aqueous methanol as eluant and character- ized by TLC and mass spectrometry. In this manner compounds with alky groups varying in length from $C_{12}$ to $C_{18}$ were synthesized.

EXAMPLE 3

Formulation of Cationic Lipids into Liposomes

In general the required amount of the cationic lipid and the co-lipid are weighed and transferred into a round bottom flask. An amount of chloroform that is enough to dissolve the lipids is added followed by sufficient molecular biology grade water to make the desired concentration of total lipids/volume (e.g. 2 mg/ml). The solution is placed on the rotary evaporator and the chloroform removed under vacuum. As the chloroform is removed, liposomes are formed in the aqueous medium. The solution becomes opalescent and varies in its turbidity depending on the cationic lipid and co-lipid being formulated. For example 10.4 mg of 1,4-bis[(3-amino-2-hydroxy-propyl)-tetradecyl-amino]-butane-2,3-diol and 9.6 mg of DOPE (1:1 molar ratio) were combined and placed in a round bottom flask. The lipid mixture was dissolved in 2 ml of chloroform. 10 ml of water was added to the chloroform solution. The chloroform was removed under vacuum on the rotary evaporator to obtain a liposome solution of 2 mg/ml (MT-R1). Similarly N-1-dimethyl-N-1-(2,3-ditetradecyloxypropyl)-2-hydroxypropane-1,3-diamine was formulated with DOPE (1:1) (MT-R2) and N-1-dimethyl-N-1-(2,3-ditetradecyloxypropyl)-2-(3-amino-2-hydroxypropyloxy)-propane-1,3-diamine was formulated into a liposome by itself (MT-R3) as well as with DOPE.

EXAMPLE 4

Transfection Protocol

Transfection of BHK-21, HeLa, COS-7, CHO-K1, VERO and 293 with β-galactosidase reporter plasmid pCMV●SPORT-β-gal was carried out as follows:

Cells were plated in a 96-well plates with 100 µl of media containing 10% fetal calf serum the day before transfection such that a desired confluency (70%-95%) was achieved. The following day lipid and DNA were mixed in Opti-MEM to form DNA/lipid complexes. Complexes were formed by adding various amounts of lipids (0.1 to 1.0 µl) to 100 µl of Opti-MEM. DNA (50 ng to 400 ng) was added to 100 µl Opti-MEM. The DNA and lipids solutions were then mixed to form DNA lipid complexes. The complexes were incubated at least for 20 minutes and 20 µl of complexes were added directly to the cells in 10% serum. Cells were incubated for an additional 24 hours to allow expression of the plasmid. Medium was removed and the cells were lysed in 100-200 µl of lysis buffer. The lysates (20 µl) were assayed for β-gal activity using the enzymatic substrate ONPG. Total activity was determined by reading the OD at 405 using Bio-Rad Benchmark Microplate Spectrophotometer.

For siRNA transfection, a 24 well plate is seeded with the appropriate number of cells in serum containing medium a day before transfection such that they will be 50 to 60% confluent and incubated at 37° C. in a 3-5% $CO_2$ incubator overnight. For each well to be transfected 25 µl of serum free medium containing 0.2 to 0.4 µl of lipid and 25 µl of serum-free medium containing siRNA is prepared. Final concentration of siRNA is 10 nM. The lipid and siRNA solutions are mixed and incubated at room temperature for 20 minutes. The lipid/siRNA complex (50 µl) is added to the cells in serum containing medium and the cells are incubated at 37° C. in $CO_2$ incubator. Gene silencing can be monitored at 24 to 72 hours after transfection.

Figure 2:
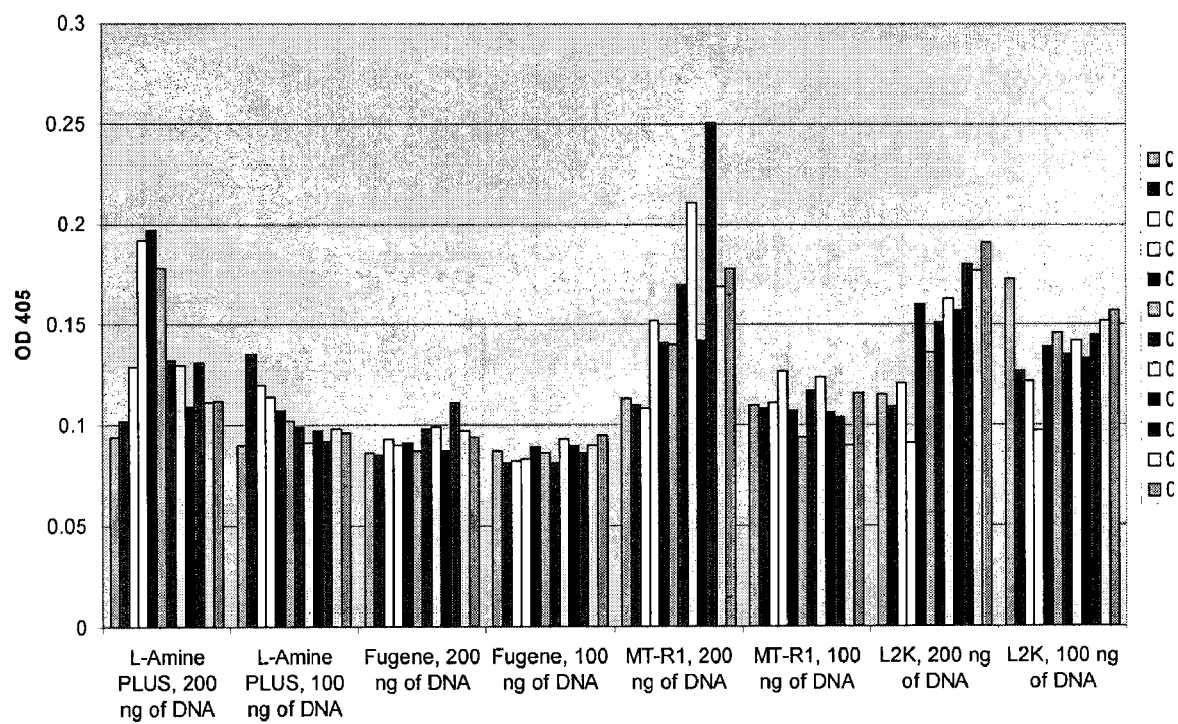
FIG. 2 shows the results obtained from transfection of VERO cells with pCMV-Sport β-gal using MT-R1 and commercial cationic lipids.
Figure 3:
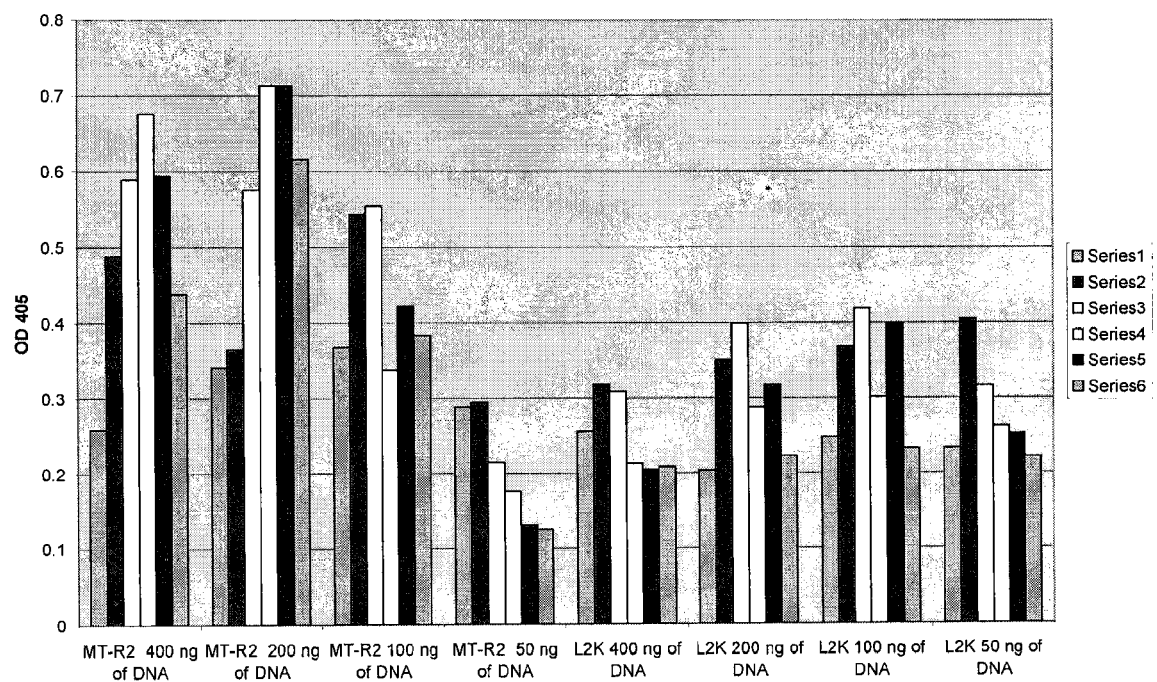
FIG. 3 shows the results obtained from transfection of BHK-21 cells with pMCMV-Sport β-gal MT-R2 and lipofectamine 2000.

Representative results are shown in FIGS. 1-3 below.

What is claimed is:

1. A lipid having the formula:

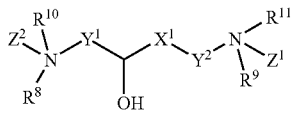

wherein $X^1$ is selected from the group consisting of $(CH_2)_n$, $(CHOH)_n$, —NH—, —O—, a polyether, an ester linkage —S—, CONH, NHCO, a polyamide —NHCONH—, and NHC (=NH) NH, $Y^1$ is selected from the group consisting of $(CH_2)_n$, a polyether, NHCO, —CO—, and a polyamide, $Y^2$ is selected from the group consisting of $(CH_2)_n$, —NH—, —O—, a polyether, an ester linkage, —S—, CONH, NHCO, a polyamide —NHCONH—, and NHC (=NH) NH, $Z^1$ and $Z^2$ are independently selected from the group consisting of primary alkylamine, secondary alkylamine, tertiary alkyl amine, quaternary alkylamine, alkyl amino alcohol, alkyl polyamine, spermidine, spermine, carboxy spermine, guanidinium, pyridinium, pyrollidinium, piperidinyium amino acyl, peptidyl, and protein, $R^8$ and $R^9$ are independently selected from the group consisting of straight chain $C_1$-$C_{20}$ alkyl, branched alkyl, cycloalkyl, straight chain alkenyl, branched alkenyl, cyclo alkenyl, and optionally substituted aryl, wherein said optional substitution, when present, comprises at least one functional group selected from the group consisting of —OH, $NH_2$, —COOH, ester, amide, alkylamino, —NHCONH—, and NHC (=NH) NH], $R^{10}$ and $R^{11}$ are independently absent or selected from the group consisting of hydrogen, straight chain $C_1$-$C_{20}$ alkyl, branched alkyl, cycloalkyl, straight chain alkenyl, branched alkenyl, cyclo alkenyl, and optionally substituted aryl, wherein said optional substitution, when present, comprises at least one functional group selected from the group consisting of —OH, $NH_2$, —COOH, ester, amide, alkylamino, —NHCONH—, and NHC (=NH) NH], and n=1-12.

2. A lipid according to claim 1, wherein $R^8$ and $R^9$ are independently selected from the group consisting of straight chain $C_1$-$C_{20}$ alkyl and branched alkyl.

3. A lipid according to claim 1 wherein $X^1$ is $(CHOH)_n$.

4. A composition comprising a lipid and a macromolecule, wherein said lipid has the formula:

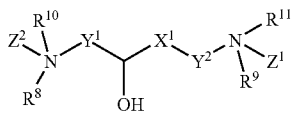

wherein $X^1$ is selected from the group consisting of $(CH_2)_n$, $(CHOH)_n$, —NH—, —O—, a polyether, an ester linkage —S—, CONH, NHCO, a polyamide —NHCONH—, and NHC (=NH) NH, $Y^1$ is selected from the group consisting of $(CH_2)_n$, a polyether, NHCO, —CO—, and a polyamide, $Y^2$ is selected from the group consisting of $(CH_2)_n$, —NH—, —O—, a polyether, an ester linkage, —S—, CONH, NHCO, a polyamide —NHCONH—, and NHC (=NH) NH, $Z^1$ and $Z^2$ are independently selected from the group consisting of primary alkylamine, secondary alkylamine, tertiary alkyl amine, quaternary alkylamine, alkyl amino alcohol, alkyl polyamine, spermidine, spermine, carboxy spermine, guanidinium, pyridinium, pyrollidinium, piperidinyium amino acyl, peptidyl, and protein, $R^8$ and $R^9$ are independently selected from the group consisting of straight chain $C_1$-$C_{20}$ alkyl, branched alkyl, cycloalkyl, straight chain alkenyl, branched alkenyl, cyclo alkenyl, and optionally substituted aryl, wherein said optional substitution, when present, comprises at least one functional group selected from the group consisting of —OH, $NH_2$, —COOH, ester, amide, alkylamino, —NHCONH—, and NHC (=NH) NH], $R^{10}$ and $R^{11}$ are independently absent or selected from the group consisting of hydrogen, straight chain $C_1$-$C_{20}$ alkyl, branched alkyl, cycloalkyl, straight chain alkenyl, branched alkenyl, cyclo alkenyl, and optionally substituted aryl, wherein said optional substitution, when present, comprises at least one functional group selected from the group consisting of —OH, $NH_2$, —COOH, ester, amide, alkylamino, —NHCONH—, and NHC (=NH) NH], and n=1-12.

5. The composition according to claim 4 wherein said macromolecule is a peptide, protein or a nucleic acid.

6. The composition according to claim 5 wherein said macromolecule is a nucleic acid.

7. The composition according to claim 6, wherein said nucleic acid comprises a DNA molecule.

8. The composition according to claim 7, wherein said DNA molecule is a double stranded DNA molecule.

9. The composition according to claim 8, wherein said DNA molecule is a plasmid.

10. The composition according to claim 9, wherein said plasmid encodes an RNA molecule that is self complementary and that forms a region of double stranded RNA.

11. The composition according to claim 6, wherein said nucleic acid comprises an RNA molecule.

12. The composition according to claim 11, wherein said RNA molecule is a double stranded RNA molecule.

13. The composition according to claim 12, wherein said RNA molecule is an siRNA.

14. A method of introducing a macromolecule into a cell, comprising contacting a eukaryotic cell with a composition comprising a lipid and a macromolecule, wherein said lipid has the formula:

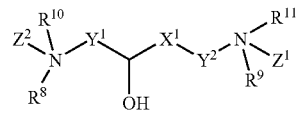

wherein $X^1$ is selected from the group consisting of $(CH_2)_n$, $(CHOH)_n$, —NH—, —O—, a polyether, an ester linkage —S—, CONH, NHCO, a polyamide —NHCONH—, and NHC (=NH) NH, Y¹ is selected from the group consisting of $(CH_2)_n$, a polyether, NHCO, —CO—, and a polyamide, Y² is selected from the group consisting of $(CH_2)_n$, —NH—, —O—, a polyether, an ester linkage, —S—, CONH, NHCO, a polyamide —NHCONH—, and NHC (=NH) NH, $Z^1$ and $Z^2$ are independently selected from the group consisting of primary alkylamine, secondary alkylamine, tertiary alkyl amine, quaternary alkylamine, alkyl amino alcohol, alkyl polyamine, spermidine, spermine, carboxy spermine, guanidinium, pyridinium, pyrollidinium, piperidinyium amino acyl, peptidyl, and protein, $R^8$ and $R^9$ are independently selected from the group consisting of straight chain $C_1$-$C_{20}$ alkyl, branched alkyl, cycloalkyl, straight chain alkenyl, branched alkenyl, cyclo alkenyl, and optionally substituted aryl, wherein said optional substitution, when present, comprises at least one functional group selected from the group consisting of —OH, $NH_2$, —COOH, ester, amide, alkylamino, —NHCONH—, and NHC (=NH) NH], $R^{10}$ and $R^{11}$ are independently absent or selected from the group consisting of hydrogen, straight chain $C_1$-$C_{20}$ alkyl, branched alkyl, cycloalkyl, straight chain alkenyl, branched alkenyl, cyclo alkenyl, and optionally substituted aryl, wherein said optional substitution, when present, comprises at least one functional group selected from the group consisting of —OH, $NH_2$, —COOH, ester, amide, alkylamino, —NHCONH—, and NHC (=NH) NH], and n=1-12.

15. A composition according to claim 5 wherein said macromolecule is a peptide or protein.

16. A method according to claim 14, wherein said macromolecule is a nucleic acid.

17. A method according to claim 14, wherein said macromolecule is a peptide or protein.

18. A method of introducing a desired molecule into a tissue, comprising contacting said tissue with a composition comprising said desired molecule and a lipid, wherein said lipid has the formula:

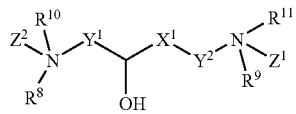

wherein $X^1$ is selected from the group consisting of $(CH_2)_n$, $(CHOH)_n$, —NH—, —O—, a polyether, an ester linkage —S—, CONH, NHCO, a polyamide —NHCONH—, and NHC (=NH) NH, Y¹ is selected from the group consisting of $(CH_2)_n$, a polyether, NHCO, —CO—, and a polyamide, Y² is selected from the group consisting of $(CH_2)_n$, —NH—, —O—, a polyether, an ester linkage, —S—, CONH, NHCO, a polyamide —NHCONH—, and NHC (=NH) NH, $Z^1$ and $Z^2$ are independently selected from the group consisting of primary alkylamine, secondary alkylamine, tertiary alkyl amine, quaternary alkylamine, alkyl amino alcohol, alkyl polyamine, spermidine, spermine, carboxy spermine, guanidinium, pyridinium, pyrollidinium, piperidinyium amino acyl, peptidyl, and protein, $R^8$ and $R^9$ are independently selected from the group consisting of straight chain $C_1$-$C_{20}$ alkyl, branched alkyl, cycloalkyl, straight chain alkenyl, branched alkenyl, cyclo alkenyl, and optionally substituted aryl, wherein said optional substitution, when present, comprises at least one functional group selected from the group consisting of —OH, $NH_2$, —COOH, ester, amide, alkylamino, —NHCONH—, and NHC (=NH) NH], $R^{10}$ and $R^{11}$ are independently absent or selected from the group consisting of hydrogen, straight chain $C_1$-$C_{20}$ alkyl, branched alkyl, cycloalkyl, straight chain alkenyl, branched alkenyl, cyclo alkenyl, and optionally substituted aryl, wherein said optional substitution, when present, comprises at least one functional group selected from the group consisting of —OH, $NH_2$, —COOH, ester, amide, alkylamino, —NHCONH—, and NHC (=NH) NH], and n=1-12.

19. The method according to claim 18 wherein said desired molecule is a peptide, protein, or nucleic acid.

20. A kit for transfecting a cell, comprising a lipid having the formula

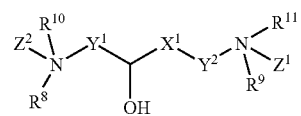

wherein $X^1$ is selected from the group consisting of $(CH_2)_n$, $(CHOH)_n$, —NH—, —O—, a polyether, an ester linkage —S—, CONH, NHCO, a polyamide —NHCONH—, and NHC (=NH) NH, Y¹ is selected from the group consisting of $(CH_2)_n$, a polyether, NHCO, —CO—, and a polyamide, Y² is selected from the group consisting of $(CH_2)_n$, —NH—, —O—, a polyether, an ester linkage, —S—, CONH, NHCO, a polyamide —NHCONH—, and NHC (=NH) NH, $Z^1$ and $Z^2$ are independently selected from the group consisting of primary alkylamine, secondary alkylamine, tertiary alkyl amine, quaternary alkylamine, alkyl amino alcohol, alkyl polyamine, spermidine, spermine, carboxy spermine, guanidinium, pyridinium, pyrollidinium, piperidinyium amino acyl, peptidyl, and protein, $R^8$ and $R^9$ are independently selected from the group consisting of straight chain $C_1$-$C_{20}$ alkyl, branched alkyl, cycloalkyl, straight chain alkenyl, branched alkenyl, cyclo alkenyl, and optionally substituted aryl, wherein said optional substitution, when present, comprises at least one functional group selected from the group consisting of —OH, $NH_2$, —COOH, ester, amide, alkylamino, —NHCONH—, and NHC (=NH) NH], $R^{10}$ and $R^{11}$ are independently absent or selected from the group consisting of hydrogen, straight chain $C_1$-$C_{20}$ alkyl, branched alkyl, cycloalkyl, straight chain alkenyl, branched alkenyl, cyclo alkenyl, and optionally substituted aryl, wherein said optional substitution, when present, comprises at least one functional group selected from the group consisting of —OH, $NH_2$, —COOH, ester, amide, alkylamino, —NHCONH—, and NHC (=NH) NH], and n=1-12.

21. A lipid having the formula:

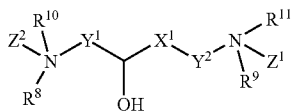

wherein $X^1$ is $(CHOH)_n$,
$Y^1$ is $(CH_2)_n$,
$Y^2$ is $(CH_2)_n$,
$Z^1$ and $Z^2$ are independently selected from the group consisting of primary alkylamine, secondary alkylamine, tertiary alkyl amine, quaternary alkylamine, alkyl amino alcohol, alkyl polyamine, spermidine, spermine, and carboxy spermine,
$R^8$ and $R^9$ are independently selected from the group consisting of straight chain $C_1$-$C_{20}$ alkyl, branched alkyl, cycloalkyl, straight chain alkenyl, branched alkenyl, and cyclo alkenyl,
$R^{10}$ and $R^{11}$ are independently absent or hydrogen, and
n=1-12.

22. A lipid according to claim 21, wherein $Z^1$ and $Z^2$ are independently selected from the group consisting of primary alkylamine, secondary alkylamine, tertiary alkyl amine, quaternary alkylamine, and alkyl amino alcohol.

23. A lipid according to claim 21, wherein $R^8$ and $R^9$ are independently selected from the group consisting of straight chain $C_1$-$C_{20}$ alkyl, and branched alkyl.

24. A lipid according to claim 21, wherein $R^8$ is a long chain alkyl.

25. A composition comprising a lipid and a nucleic acid, wherein said lipid is a lipid according to claim 21.

26. A method of introducing a nucleic acid into a cell, comprising contacting a eukaryotic cell with a composition comprising a lipid and said nucleic acid, wherein said lipid is a lipid according to claim 21.

27. A method of introducing a nucleic acid into a tissue, comprising contacting said tissue with a composition comprising said nucleic acid and a lipid, wherein said lipid is a lipid according to claim 21.

* * * * *